United States Patent
Alaluf et al.

(10) Patent No.: US 6,365,175 B1
(45) Date of Patent: Apr. 2, 2002

(54) PETROSELINIC ACID AND ITS USE IN FOOD

(75) Inventors: Simon Alaluf; Martin Richard Green; Jonathan Richard Powell; Julia Sarah Rogers; Allan Watkinson, all of Shambrook (GB); Frederick William Cain, Wormerveer (NL); Heng Long Hu, Abbeymead; Anthony Vincent Rawlings, Bebington, both of (GB)

(73) Assignee: Unilever Patent Holdings, Vlaardingen (NL)

(*) Notice: Subject to any disclaimer, the term of this patent is extended or adjusted under 35 U.S.C. 154(b) by 0 days.

(21) Appl. No.: 09/468,636

(22) Filed: Dec. 22, 1999

(30) Foreign Application Priority Data

Dec. 22, 1998 (EP) .............................................. 98310626
Dec. 22, 1998 (EP) .............................................. 98310627
Mar. 17, 1999 (EP) .............................................. 99302067

(51) Int. Cl.⁷ ......................... A61K 47/00; A61K 31/74
(52) U.S. Cl. ................... 424/439; 424/78.05; 514/786; 514/787
(58) Field of Search .............................. 424/439, 78.05; 514/473, 557, 786, 787

(56) References Cited

U.S. PATENT DOCUMENTS

| | | | | |
|---|---|---|---|---|
| 4,918,063 A | | 4/1990 | Lictenberger | 514/78 |
| 5,242,945 A | * | 9/1993 | Caufield et al. | 514/473 |
| 5,605,929 A | | 2/1997 | Liao et al. | 514/456 |
| 6,022,896 A | * | 2/2000 | Weinkauf et al. | 514/557 |

FOREIGN PATENT DOCUMENTS

| | | | |
|---|---|---|---|
| EP | 777971 | * | 6/1997 |
| EP | 0 777 971 A1 | | 6/1997 |
| EP | 777971 A | * | 6/1997 |
| JP | 61257944 | | 11/1986 |
| WO | WO 95/00136 | | 1/1995 |

OTHER PUBLICATIONS

Afifi et al., "Some pharmacological activities of essential oils of certain umbelliferous fruits", VET. MED. J. GIZA, vol. 42, No. 3, 1994, pp 85–92.*
Afifi et al., "Some pharmacological activities of essential oils of certain umbelliferous fruits", VET. MED. J. GIZA, vol. 42, No. 3, 1994, pp 85–92.*
Yagaloff, "Essential fatty acids are antagonists of the leukotriene B4 receptor", Prostaglandins, Leukotriens and Essential Fatty Acids, vol. 52, 1995, pp 293–297.*
Patent Abstracts of Japan, Publication No. 61181352.
Yagaloff et al, Prostaglandins Leukotrienes and Essential Fatty Acids, 52(5):293–297 (1995) (XP 002050601).
Afifi et al, Vet. Med. J. Giza., 42(3):85–92 (1994) (XP 002050599).
Derwent Abstract XP–002120504.
Derwent Abstract XP–002120503.

* cited by examiner

Primary Examiner—Thurman K. Page
Assistant Examiner—Blessing Fubara
(74) Attorney, Agent, or Firm—Morgan, Lewis & Bockius LLP

(57) ABSTRACT

Edible compositions containing petroselinic acid are used for the preparation of food compositions or food supplements that are used as anti-inflammatory compositions that inhibit the production of metabolites of arachidonic acid and/or reduces the formation of intracellular adhesion molecules or as anti-aging compositions with a positive impact on wrinkling, sagging, photodamaged skin, dry skin, flaky skin and age spots.

22 Claims, 6 Drawing Sheets

Inhibition of PMA-induced PGE2 production by petroselinic acid in a fibroblast cell model.

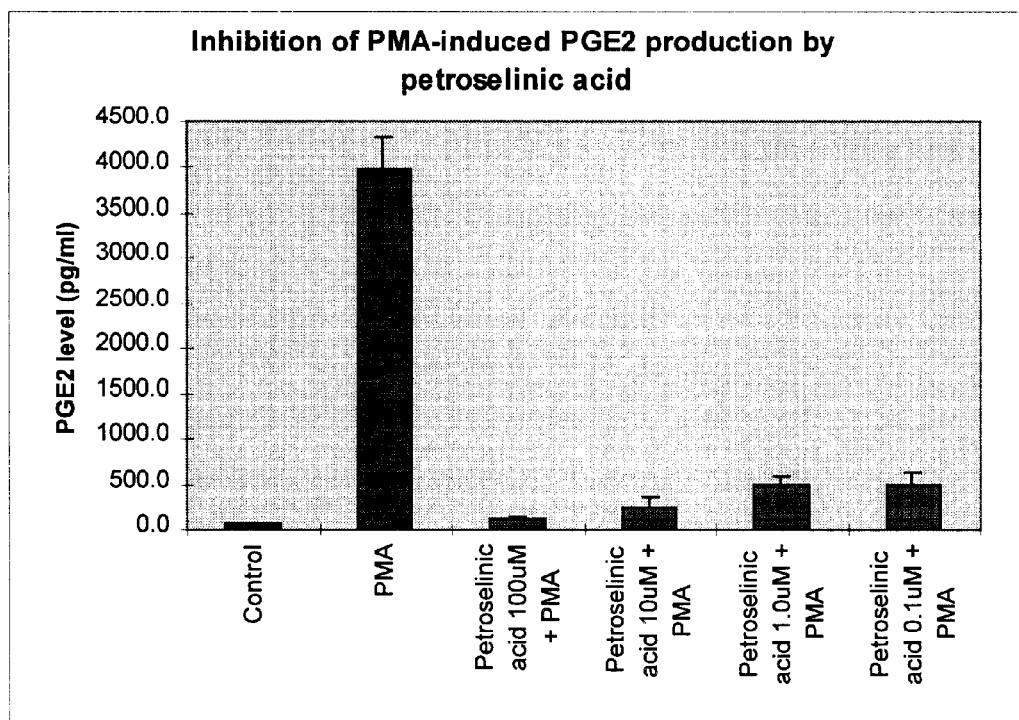
Figure 1. Inhibition of PMA-induced PGE2 production by petroselinic acid in a fibroblast cell model.

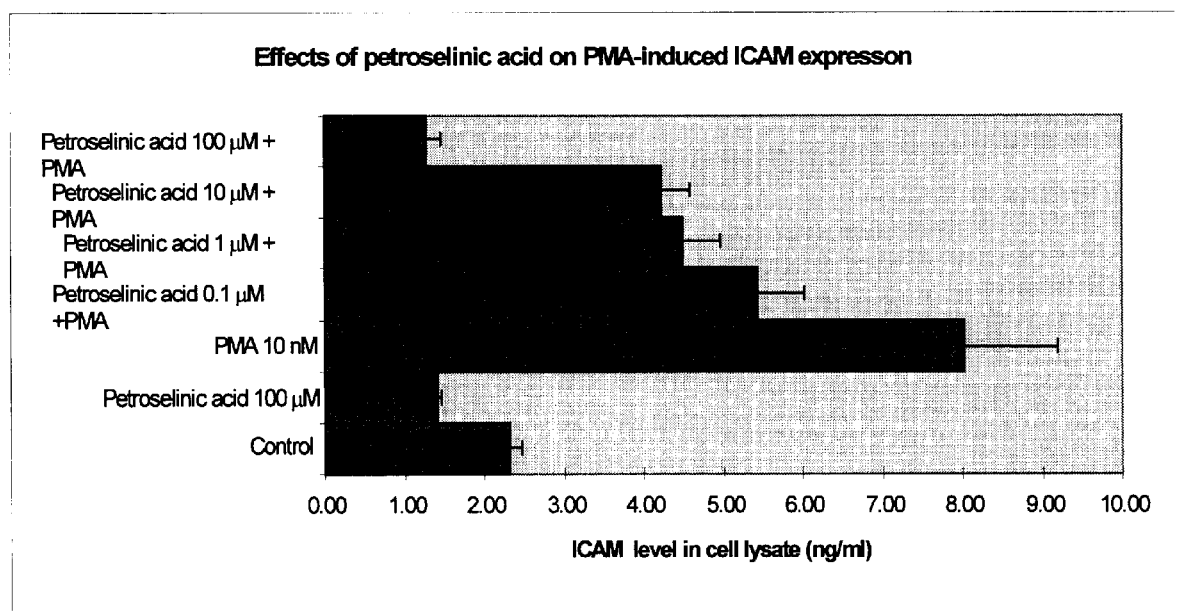
Figure 2. Inhibition of PMA-induced ICAM production by petroselinic acid in a fibroblast cell model.

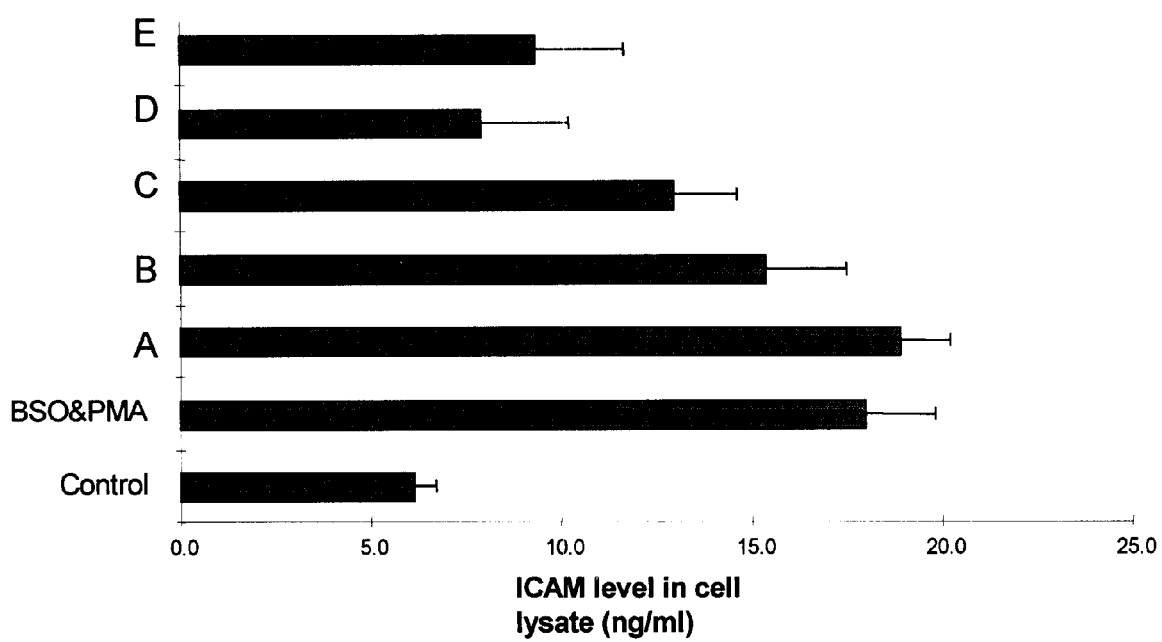
Figure 3. Inhibition of PMA and BSO induced ICAM production by petroselinic acid and antioxidants in a fibroblast cell model.

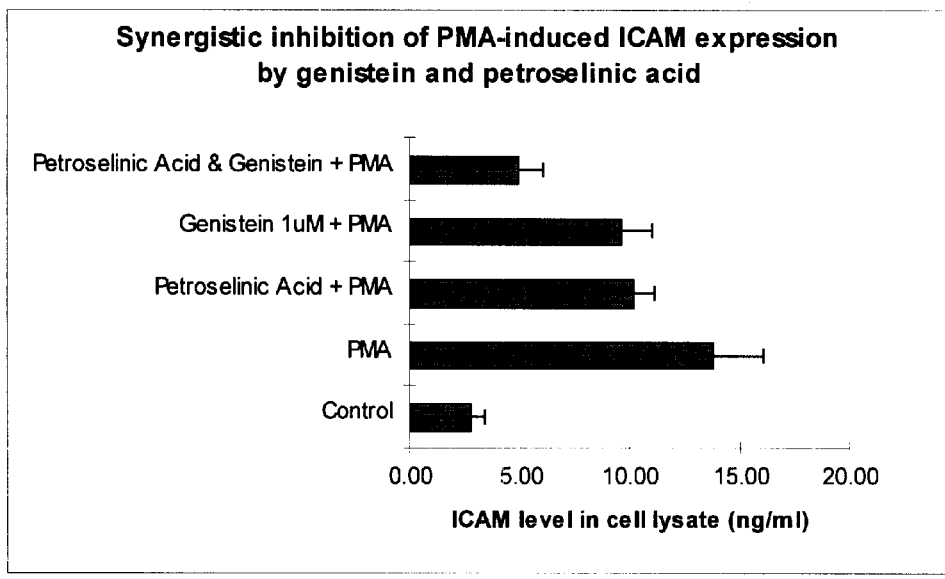
Figure 4. Inhibition of PMA induced ICAM production by petroselinic acid and genistein in a fibroblast cell model.

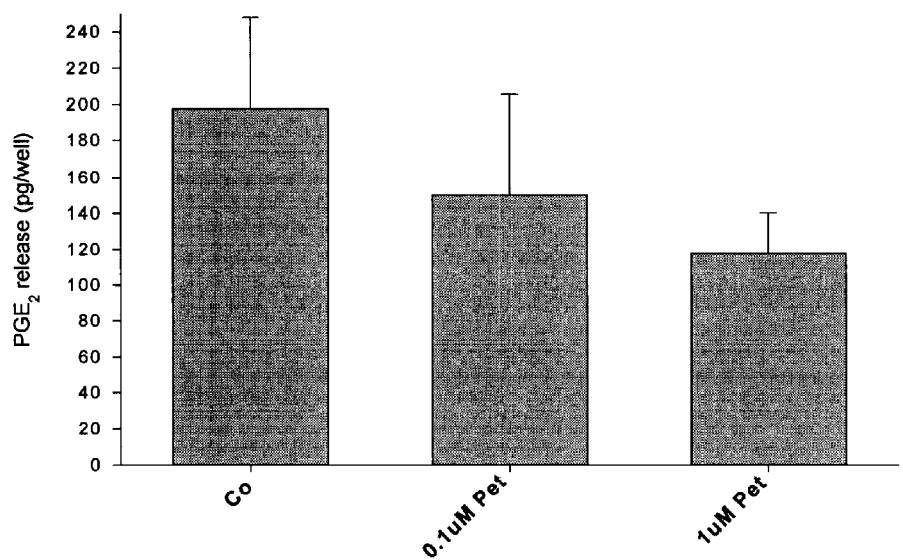
Figure 5. Inhibition of keratinocyte PGE2 by petroselinic acid.

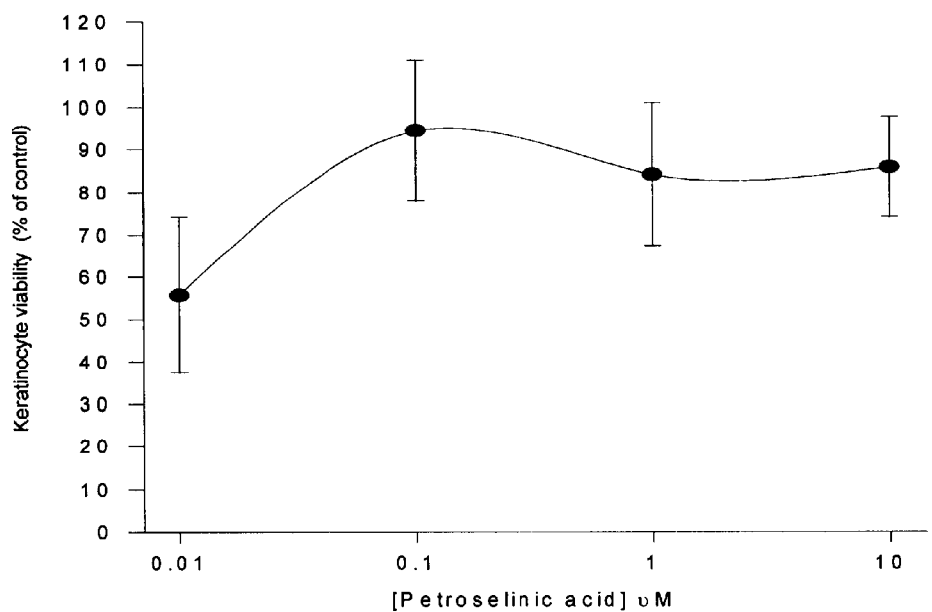
Figure 6. Protection of keratinocytes in presence of SDS.

PETROSELINIC ACID AND ITS USE IN FOOD

FIELD OF THE INVENTION

The invention relates to edible compositions containing petroselinic acid for anti-inflammatory and/or anti-aging use. Petroselinic acid is a well known compound that eg is present in coriander oil in relatively high amounts. Its use in food products is also disclosed in literature. EP 777971 eg discloses that fat compositions can be obtained from fats that have high contents of asymmetric monounsaturated fatty acids, such as petroselinic acid, ie PSA (>79 wt %) and that have simultaneously low contents of trans acids (<5 wt %). The fat compositions obtained can be used as fat replacer with a number of benefits such as providing good textural properties to the food, while not raising the LDL-cholesterol levels in the blood serum. When considering example 5, in particular table 3 of this patent application one must conclude that good product performance is only obtained if the fat applied contains about 12 wt % PSA. Products based on fats without PSA perform badly (=control fat 1). Fats with only small amounts PSA are still grainy, while using a fat with a high content of PSA (=fat 4 with about 64 wt % PSA via the coriander oil) has a poor overall appearance. Food products that are indicated are margarines, dressings, confections, spreads, frozen desserts, ice cream, mayonnaise, mustards, cheese, dip sauces, bread, biscuit, dairy products, frying oils, CBE's, candy, meat, egg products, nut products, vegetable or fruit products, toppings, creams, puddings, cookies, pastries, pies, crackers, cakes, bread rolls and ingredients or premixes herefore. As PSA is the active ingredient that provides the health benefits to the food product there is a big need to be able to use fats with high levels of PSA but that perform well when applied in food products. Ie the appearance of the food products should be good as well.

Inflammation is a key problem in a number of disease states. Extensive scientific research has focused on identifying compounds that have anti-inflammatory activity. So far the main treaments are synthetic compounds in the pharmaceutical area or complex mixtures of compounds, synthetic or natural. It is known that fish oils can be used to some extent as an anti-inflammatory. However, fish oils have the disadvantage of being very unstable and of forming off tastes very easily. Therefore the use of products based on fish oils as anti-inflammatory compositions has not found wide commercial application within the public domain.

U.S. Pat. No. 4,918,063 (1990) discloses that some specific inflammatory diseases such as peptic ulcer disease or inflammatory bowel disease can be prevented or treated with mixtures of saturated or unsaturated phospholipids and saturated or unsaturated triglycerides and/or sterols. The activity of these mixtures is attributed to the fact that these mixtures have the ability to increase or maintain its hydrophobic character by treating the luminal surface of the gastrointestinal tract. It is expressly disclosed that the use of unsaturated phospholipids per se does not work. These compounds only can work in the presence of a triglyceride or sterol. This thus leads away from using unsaturated derivatives of fatty acids for the purposes mentioned in this document. No examples are given for the use of petroselinic acid or glycerides containing this. The only indication herefore can be found in a listing in table 1.

The teaching laid down in the above U.S. 063 is confirmed by U.S. Pat. No. 5,178,873, wherein a method for inhibiting phospholipase A2 activity is disclosed by using stearidionic acid or a C20:4 unsaturated fatty acid. In the Tables 2 and 3 it is demonstrated in a comparative example that petroselinic acid is not useful for this purpose.

Another well recognized consumer problem is formed by the aging of the skin. In recent years the demand for methods to improve the appearance of skin and, in particular, for reducing or preventing the visible signs of wrinkled, aged and/or photodamaged skin has grown enormously. It is known in the art that the levels of collagen, a dermal structural protein and decorin, a structuring proteoglycan in skin are significantly reduced with aged and/or photodamaged skin (Lavker et al J.Inv.Derm.1979 73:79–66, Bernstein et al Lab. Invest. 1995 72:662–669). The reduction in these proteins is associated with a decrease in the tensile strength of the skin causing wrinkles and laxity.

Extensive research has focused on identifying actives that have anti-aging activity. One of the main current actives is retinoic acid, giving wrinkle effacement and dermal repair through boosting for example by collagen synthesis (e.g. Griffiths et al. N. Eng. J. med. 1993 329:530–535). According to GB 2 181 349 another solution was found in the use of triglycerides derived from long chain polyunsaturated fatty acids in cosmetic or dermatological compositions. These compositions are thus not edible in general because they also will contain non edible components. Moreover the triglycerides derived from these polyunsaturated fatty acids are unstable in particular with respect to oxygen stability.

We studied whether we could find a natural component that could be used as anti-inflammatory agent without creating problems of side effects and not having the negative aspects from fish oils, and other known anti-inflammatory compositions.

We also studied whether we could find a natural component that could be used as anti-aging agent without creating problems of side effects and not having the negative aspects from the known anti-aging compositions.

We further studied whether we could find fat compositions that combine high PSA levels with a very good product performance.

The study on anti-inflammatory and antiaging activity resulted in our finding that petroselinic acid derivatives (ie free fatty acid, short alkyl ester, short being C1–C4, waxesters, mono-di- or triglycerides) can be applied as firstly anti-inflammatory agents that act on the formation of metabolites from arachidonic acid (a recognised precursor of inflammatory mediators), or that can reduce the formation of intracellular adhesion molecules, and thus contribute to the inflammatory response. Or secondly can be applied as an anti-aging agent that act by boosting the levels of two structural proteins in the dermis of the skin, collagen and decorin. Moreover we found novel fat compositions that combine high PSA levels with good product performance.

BRIEF SUMMARY OF THE INVENTION

Therefore our invention concerns in the first instance the use of edible compositions containing petroselinic acid for the preparation of functional food compositions or food supplements, wherein the composition containing petroselinic acid is used as an anti-inflammatory component that inhibits the production of metabolites of arachidonic acid and/or reduces the formation of intracellular adhesion molecules.

Our invention further concerns the use of edible compositions containing petroselinic acid for the preparation of functional food compositions or food supplements, wherein the composition containing petroselinic acid is used as an anti-aging component that boosts decorin levels with a positive impact on skin conditions selected from the group consisting of wrinkling, sagging, photodamaged skin, dry skin, flaky skin and age spots.

Functional food compositions being defined as food compositions containing at least one component with a health benefit. Food supplements being defined as compositions that are not used as food per se, but that are used as supplement to the daily food intake, in general in the form of encapsulated essential food ingredients. These edible compositions containing petroselinic acid can be applied in many different forms, but we prefer to apply these compositions as a composition comprising 5–99.9 wt % of fat or fat blend.

The fats that can be used in the compositions containing the petroselinic acid derivative can be selected from the group consisting of: cocoa butter equivalents, palm oil or fractions thereof, palm kernel oil or fractions thereof, interesterified mixtures of above fats, hardened fats or fractions thereof, liquid oils, selected from sunflower oil, high oleic sunflower oil, soybean oil, rape seed oil, cotton seed oil, safflower oil, high oleic safflower oil, maize oil, MCT oils, hardened liquid oils or fractions thereof and mixtures hereof.

These fats are nearly all natural fats (the exception being MCT oils which are synthetic fats based on medium chain fatty acids ie fatty acids with 6–12 carbon atoms). The level of petroselinic acid in the compositions that we can apply for our purposes can vary widely, however we prefer to apply petroselinic acid containing compositions that contain 2–80 wt %, preferably 5–40 wt % of petroselinic acid derivative (calculated as petroselinic acid).

As already indicated above we found that the petroselinic acid could be used in different forms. Very good results were obtained by using the petroselinic acid as free fatty acid, or in a form wherein it is bound to a glycerol backbone as in mono-di- or triglycerides. In this latter case the glycerides must contain at least one petroselinic acid moiety. Other forms are short alkyl esters of the petroselinic acid, short meaning having one to eight, preferably 1 to 4 carbon atoms. Also wax esters, i.e. long chain alcohol esters of petroselinic acid can be applied. Of course also mixtures of above forms can be used.

We also found that the anti-inflammatory and antiaging effect of the petroselinic acid can be increased, even in a synergistic way by using the petroselinic acid derivative in combination with one or more anti-oxidants. Typical examples of useful anti-oxidants can be selected from the group consisting of natural or synthetic tocopherols, natural polyphenols, in particular as present in tea extracts, BHT, BHA, free radical scavengers and enzymes with anti-oxidant properties. From these anti-oxidants we prefer the tocopherols and the polyphenols as present in tea extracts the most.

The petroselinic acid derivatives will structure the fats when applied in a fat surrounding. Therefore structured fats comprising the petroselinic acid composition and wherein the fat has a level of saturated plus trans fatty acids of 25–75 wt % are also part of our invention.

Part of the invention are also the blends of the petroselinic acid containing composition and 0.01–5 wt % of one or more anti-oxidants selected from the group consisting of: natural or synthetic tocopherols, natural polyphenols, in particular as present in tea extracts, BHT, BHA, free radical scavengers and enzymes with anti-oxidant properties.

Food products or food supplements containing these blends are also part of our invention. As food products all food products indicated in EP 777971 could be used.

A very useful form wherein the active petroselinic acid or derivative can be applied is an encapsulated composition, wherein the petroselinic acid is encapsulated in an edible encapsulating material. The encapsulating material is selected from the group consisting of: polysaccharides, sugars, fats, proteins and amino acids.

The encapsulating material is present in an amount of 5–95 wt % on basis of total encapsulated composition.

These encapsulated forms are in general free flowing which makes the dosing of the food products or food supplements easier.

As a result of our study to find fat compositions that combine high PSA levels with very good product performance we found that fat compositions comprising asymmetric isomers from cis monounsaturated fatty acids, wherein the fat composition comprises 15–75 wt %, preferably 20–60 wt %, most preferably 30–60 wt % of asymmetric isomers from cis monounsaturated fatty acids preferably being petroselinic acid, 25–50 wt %, preferably 30–40 wt % of saturated fatty acids with 12–24 carbon atoms and 0–60 wt %, preferably 5–50 wt %, most preferably 15–45 wt % of isomers of other fatty acids with at least 18 carbon atoms, preferably having a cis 9 double bond, preferably being oleic acid, or linoleic acid, are very suitable for this purpose.

BRIEF DESCRIPTION OF THE DRAWINGS

FIG. 1 illustrates the inhibition of PMA-induced PGE2 production by petroselinic acid in a fibroblast cell model.

FIG. 2 illustrates the inhibition of PMA-induced ICAM production by petroselinic acid in a fibroblast cell model.

FIG. 3 illustrates the inhibition of PMA and BSO induced ICAM production by petroselinic acid and antioxidants in a fibroblast cell model.

FIG. 4 illustrates the inhibition of PMA-induced ICAM production by petroselinic acid and genistein in a fibroblast cell model.

FIG. 5 illustrates the inhibition of keratinocyte PGE2 by petroselinic acid.

FIG. 6 illustrates the protection of keratinocytes in presence of SDS.

DETAILED DESCRIPTION OF THE INVENTION

According to a preferred embodiment of this aspect of our invention these compositions comprise three components A, B and C, wherein:

A has a content of asymmetric isomers from monounsaturated fatty acids of at least 20 wt %, preferably at least 40 wt %, most preferably at least 50 wt %

B has a solid fat content, measured on a unstabelized fat by NMR, at 20° C. of at least 20, preferably at least 45, most preferably at least 60 and C has a content of fatty acids with at least 18 C atoms and a cis 9 double bond of at least 40 wt %, while components A, B and C are present in amounts of:

15–90 wt % of A, preferably 20–75 wt %, most preferably 30–50 wt %

10–85 wt % of B, preferably 20–75 wt %, most preferably 30–60 wt % and

0–75 wt %, preferably 5–60 wt %, most preferably 15–50 wt % of C.

Even more preferred compositions are obtained when the composition contains an additional fat component D in an amount of 5–60 wt %, which component D is an interesterified mixture of fats A and B in a weight ratio of 95:5–5:95. This then results in fat compositions, wherein the components A,B,C and D are present in amounts of:

5–75 wt % of A
15–60 wt % of B
5–75 wt % of fat C and
5–75 wt % of fat D.

In order to achieve the best mouth feel our fat compositions have a solid fat content unstabilised at 5° C. of 25–85, preferably 30–50 and at 35° C. of less than 10, preferably less than 5. These solid fats contents are measured by NMR pulse techniques on a fat at measurement temperature. The value for the solid fat content depends on the pretreatment of the fat. Here the solid fat content is measured on a fat that is not stabilised. I.e. the fat was melted and kept at 60° C. for 30 min, after which the fat is cooled to 0° C. and kept hereon for another 30 min, whereupon the fat is heated to measurement temperature and the solid fat index is measured after keeping the fat at this temperature for at least 1 hour.

As a source for the PSA, coriander seed oil is very useful. Coriander oil can contain up to about 80 wt % of PSA. Other fats relatively rich in PSA that can be applied as well are: parsley oil; and a number of fungal oils. PSA can also be obtained from carrots, fennel: chervil or caraway. The content of cis 6 isomers of asymmetric monounsaturated fatty acids in fats having intermediate levels thereof can be increased by performing an enzymic conversion on a fat containing at least 5 wt % of cis 6 isomers of fatty acids of monounsaturated fatty acids and containing also cis 9 double bonds using an enzyme specific for cis 9 double bonds and removing the products enriched in cis 9 double bonds. Enzymes suitable for this conversion are well known, an example being Geotrichum candidum.

Although the trans content of our fat compositions can be very low (ie <5 wt %) we can also make fat compositions with a very good performance if the trans content is 10–70 wt %. Herefore we can use partially hardened fats as fat component B or D. However low trans contents are in general preferred.

Fat B that can be applied in making our fat compositions can be selected from the group consisting of palm oil mid, palm oil stearin, cocoa butter and fully or partially hardened vegetable oils, like fully hardened bean oil, rape seed oil or cotton seed oil.

Fat C is suitably selected from the group consisting of sunflower oil, high oleic sunflower oil, olive oil, bean oil, safflower oil, rape seed oil, palm oil olein, olein fractions of vegetable oils, high oleic vegetable oils; corn oil; cotton seed oil.

Part of our invention are also the food products with a fat phase containing or consisting of the fat composition according to our invention.

Examples of food products, wherein our novel fats can be applied are: margarines; spreads; ice-creams; confectionery products (in particular fillings), bakery products (cakes, puff-pastries, laminated products etc.), cream alternatives, mayonnaises, dressings, soups and sauces. In these products the following benefits can be achieved: Higher SV in cakes and laminated products: higher patty heights in puff-pastries: better aerated batters for cake: improved overrun and stand-up properties for cream alternatives, as well as shorter whip-times herefore and better melt-down and aeration preperties for confectionery fillings.

EXAMPLES

Methodology

Anti-inflammatory Cell Assays

It is emphasized that the anti-inflammatory effects were determined by in vitro tests wherein the production of intracellular adhesion molecules (=ICAM) and Prostaglandin E2 (=PGE2) production by the human skin fibroblasts is measured after being induced by the inflammatory modulus phorbyl myristyl acetate (PMA). Effects on basal PGE2 levels in keratinocytes are also measured. A reduction of the levels of ICAM and PGE2 is indicative for the anti-inflammatory effect.

Fibroblast Cell Assay

Primary human foreskin fibroblasts at passage 2 (P2) were seeded into 96-well plates at 10000 cells/well and maintained for 24 hours in an atmosphere of 5% carbon dioxide in Dulbeccos Modified Eagles Medium (DMEM) supplemented with 10% foetal calf serum. Petroselinic acid was added to fresh cell media (DMEM, supplemented with 10% foetal calf serum) in dimethylsulphoxide (DMSO, final concentration 1%) in triplicate and incubated for a further 24 hours. Phorbal myristate acetate (PMA) in ethanol/cell media (10 nm) was added to the media and the cells incubated for a futher 24 hours. PMA represents an external stressor which induces oxidative stress and inflammatory responses in cells. The fibroblasts/media were then analysed as described below immediately or snap frozen in liquid nitrogen and stored at −70° C. for future analysis. The cells were then counted to ensure no effect on cell number.

Prostaglandin E2 (PGE2) Assay

Volumes of 50 µl culture medium were taken for PGE2 assay after gently shaking the culture plate. PGE2 levels in the medium were determined with a Biotrak PGE2 immunoassay kit (Amersham, UK). The assay is based on the competition between unlabelled PGE2 in the sample and a fixed quantity of horseradish peroxidase labelled PGE2 for a limited amount of fixed PGE2 specific antibody. Concentrations of unlabelled sample PGE2 are determined according to a standard curve which was obtained at the same time.

ICAM-1 Assay

Media were discarded and cells washed with Dulbecco PBS. To the washed cells, 150 µl 0.1% Triton X-100 (Sigma) was added for 3 minutes to extract ICAM from cell membrane. The extracts were transferred to Eppendoff centrifuge tubes and centrifuged at 1000 g for 2 min to remove cell debris. A volume of 100 µl supernatant was used for ICAM assay. The soluble ICAM-1 was assessed with commercially available immunoenzymometric assay kit (R&D Systems). Concentrations of ICAM-1 in the samples were determined based on parallelly running standard curve.

Glutathione (GSH) Depletion Model

The anti-inflammatory effects of petroselinic acid can also be shown using a glutathione (GSH) depletion model in fibroblasts. L-Buthionine sulfoximine (BSO, Sigma), a specific inhibitor of γ-glutamylcysteine synthetase, was used to deplete intracellular GSH levels. This depletion model is based on the natural degradation of GSH while synthesis is inhibited. BSO is added to the fibroblast cell media after 24 hours (0.25 mM), this is predissolved in DMSO (DMSO, final concentration <1%). In addition, where stated, the antioxidants Epigallocatechingallate (ECGC) and Quercetin were also added to the media after 24 h. The former was dissolved directly in the media, quercetin was initially dissolved in ethanol, this was then diluted 500 fold into the media.

Keratinocyte PGE2 Assay

Keratinocytes were grown in 96 well plates to approximately 80% confluency in keratinocyte growth medium (KGM) which was then replaced in with KGM without hydrocortisone for 24–48 h. The cells were then incubated in the presence or absence of petroselinic acid for 24 h. The medium was then removed and assayed for the pro-inflammatory $PGE_2$ content by Enzyme-linked immunoassay.

Keratinocyte SDS Viability Assay

Keratinocytes were grown in 96 well plates to approximately 80% confluency in keratinocyte growth medium (KGM) which was then replaced in with KGM without hydrocortisone for 24–48 h. The cells were then treated with a concentration of sodium do-decyl sulphate (SDS) which will produce cell viability of approximately 50% (2 $\mu$g/ml). This is done in the presence or absence of petroselinic acid. After incubating for 24 h the medium was removed and the cell viability determined by the Neutral Red method. Basically, the cells were incubated for 3 h in KGM containing 25 $\mu$g/ml neutral red after which the medium was removed and the cells were then extracted with 1 ml of 1% (v/v) acetic acid, 50% (v/v) ethanol for 30 min. The absorbance of the extract at 562 nm was determined and the viability evaluated by reference to control wells which contained neither SDS or petroselinic acid. This methodology has shown that the keratinocyte toxicity of an irritant relates to the irritancy effect of the agent in vivo (Lawrence et al Toxicol. In Vitro 10, 331–340 1996).

Procedure For Measuring Procollagen-I and Decorin Synthesis In Human Dermal Fibroblasts Preparation of Dermal Fibroblast Conditioned Medium Primary human foreskin fibroblasts at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents (petroselinic acid, EGCG and gallic acid) and vehicle controls were added to the cells in triplicate in a final volume of 0.4 ml/well fresh serum free DMEM and incubated for a further 24 hours. This fibroblast conditioned medium was either analysed immediatedly or snap frozen in liquid nitrogen and stored at −70° C. for future analysis. The cells were then counted and data from the dot-blot analysis subsequently standardised to cell number.

Dot Blot Assay For Decorin Protein in Dermal Fibroblast Conditioned Medium

Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm$^2$ in a 175 cm$^2$ flask and maintained in serum free DMEM as described above. Assay samples were subsequently applied in triplicate to a prewetted sheet of Immobilon-P transfer membrane using the 96-well Bio-Dot Apparatus from Bio-Rad as described in the manufacturers guidelines. Approximately 200 $\mu$l of medium was applied per well. The medium was allowed to filter through the membrane under gravity (30 minutes) after which the membrane was washed twice with PBS (200 $\mu$l). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for decorin analysis were blocked with 3% (w/v) bovine serum albumin (BSA)/ 0.1% (v/v) Tween 20 in phosphate buffered saline (PBS), whilst those for procollagen-I analysis were blocked with 5% (w/v) non fat dried milk powder/0.05% Tween 20 in PBS. The following day, the membranes were probed with 1:10000 dilution of primary antibodies to human decorin (rabbit polyclonal; Biogenesis) for 2 hours at room temperature. The membranes were subsequently washed with TBS/ 0.05% Tween 20 (3×5 minutes) and then incubated with 1:1000 dilution of $^{125}$I-conjugated anti-rat or anti-rabbit F(ab')2 fragments (Amersham) as required for 1 hour at room temperature. Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents on decorin and procollagen-I synthesis were determined relative to a vehicle treated control value of 100 arbitrary units.

EXAMPLES

1. Anti-inflammatory Effects in Fibroblasts

FIG. 1 demonstrates that challenging cells with an inflammatory stimulus such as PMA (Phorbol myristyl acetate) causes an increase in the inflammatory response as measured by prostaglandin E2 (PGE2) production. Petroselinic acid, even at the levels of 0.1 $\mu$M, dramatically reduces the inflammatory response as measured by PGE2 production. —good anti-inflammatory activity.

FIG. 2 demonstrates that petroselinic acid also decreases the production of Intracellular adhesion molecule (ICAM) in fibroblasts, which is another marker of inflammation. The reduction in ICAM occurs under both basal condition (control) and in cells stimulated with an inflammatory stimulus (in this case PMA).

The data for FIG. 1 represents the mean±standard deviation (n=3). The experiment being performed in triplicate to confirm the effect. The levels of PGE2 were measured in untreated cells (Control), cells treated with the inflammatory stimulus PMA (PMA) and PMA treated cells pre-incubated with 0.1, 1.0, 10, and 100 $\mu$M petroselinic acid. A significant decrease in PGE2 response was found for petroselinic acid treated cells.

The data for FIG. 2 represents the mean±standard deviation (n=3). The experiment being performed in triplicate to confirm the effect. The levels of ICAM were measured in untreated cells (Control), petroselinic acid treated cells (Petroselinic acid 100 $\mu$M), cells treated with the inflammatory stimulus PMA (PMA) and PMA treated cells pre-incubated with 0.1, 1.0, 10, and 100 $\mu$m petroselinic acid. A significant decrease in ICAM response was found for petroselinic acid treated cells.

2. Anti-inflammatory Effects—Synergy With Antioxidants

FIG. 3 demonstrates the effects of BSO and PMA on inflammation as measured by the levels of ICAM. Antioxidants decrease the ICAM response at a concentration of 10 $\mu$M quercetin and ECGC. In this case petroselinic was added to the media at the lower level of 0.01 $\mu$M and had no effect. Yet in combination, petroselinic acid had a synergistic effect with the antioxidants tested.

The data for FIG. 3 represents the mean±standard deviation (n=3). The experiment being performed in triplicate to confirm the effect. The levels of ICAM were measured in untreated cells (Control), BSO plus PMA treated cells (BSO&PMA), and cells treated with the inflammatory stimulus PMA and BSO pre-incubated with; A: petroselinic acid (0.1 $\mu$M), B: EGCG (10 $\mu$M), C: quercetin (10 $\mu$M), D: petroselinic acid plus EGCG (0.1 $\mu$M), E: petroselinic acid plus quercetin (0.1 $\mu$M+10 $\mu$M). A significant and synergistic decrease in ICAM response was found for petroselinic acid treated cells in the presence of antioxidants.

The data for FIG. 4 represents the mean±standard deviation (n=3). The levels of ICAM were measured in untreated cells (Control), PMA treated cells (PMA), and cells treated with the inflammatory stimuli PMA pre-incubated; petroselinic acid (1 μM), genistein (1 μM) and petroselinic acid plus genistein (1 μM) each). A significant and synergistic decrease in ICAM response was found.

3. Anti-inflammatory/Anti-irritancy Effects in Keratinocytes

Petroselinic acid was shown to significantly reduce the basal levels of secreted $PGE_2$ in keratinocytes, indicative of reduced inflammatory potential (FIG. 5). In addition, treatment with petroselinic acid reduces the toxic effects of SDS on keratinocytes indicating that it will reduce skin irritancy (FIG. 6).

The data for FIG. 5 represents the mean±standard deviation (n=4). The levels of PGE2 were measured in untreated cells (Co), and petroselinic acid treated cells (Pet 0.1 μM and 1 μM). The application of petroselinic acid reduced the basal levels of secreted $PGE_2$ indicative of reduced inflammatory potential. Statistical comparison of control (Co) and 1 μM petroselinic acid showed $p<0.05$ by Student's t-test.

The keratinocyte viability (FIG. 6) was measured in response to SDS (2 μg/ml) in the presence of petroselinic acid (0.01, 0.1, 1, 10 μM) and data represented as a percentage of the control (no petroselinic acid). All petroselinic acid values were significantly increased compared to the control as determined by Iway ANOVA with Student-Neumann-Kuels multiple comparison, $p<0.05$.

4. Anti-ageing Effects—Determined By Measurement of Decorin Levels and Synergy With Antioxidants Petroselinic acid has been demonstrated to boost decorin levels in fibroblasts, consistent with dermal repair and antiageing activity (Table 1). Antioxidants such as ECGC, gallic acid, diadzein and genistein can also exert this effect (Table 2). In combination, a synergistic boost in decorin levels is observed (Table 3).

TABLE 1

Boosting of decorin by petroselinic acid.
The production of decorin by fibroblasts was determined in control cells (no treatment) and petroselinic acid treated cells. The data is represented mean +/− standard deviation as decorin levels as a percentage of the control (no petroselinic acid). Each data point was determined in triplicate. All petroselinic acid values were significantly increased compared to the control.

| Petroselinic acid (μM) | Decorin (% of control) |
| --- | --- |
| 0 | 100.0 ± 13.6 |
| 1 | 137.6 ± 13.3 |
| 10 | 152.5 ± 14.2 |

| Antioxidants | Decorin (% of control) |
| --- | --- |
| EGCG (μg / ml) | |
| 0 | 100.0 ± 6.4 |
| 1 | 167.5 ± 11.8 |
| 2.5 | 188.6 ± 9.4 |
| 5 | 258.2 ± 6.1 |
| Gallic acid (μg / ml) | |
| 0 | 100.0 ± 7.0 |
| 1 | 136.9 ± 4.2 |
| 2.5 | 163.4 ± 6.5 |
| 5 | 161.8 ± 6.6 |

TABLE 2

Boosting of decorin by antioxidants
The production of decorin by fibroblasts was determined in control cells (no treatment) and antioxidant treated cells. The data is represented as mean +/− standard deviation for decorin levels as a percentage of the control (no antioxidant). All antioxidant values were significantly increased compared to the control. Each data point was determined in triplicate.

| Treatments | Decorin (% of control) |
| --- | --- |
| Control | 100.0 ± 1.2 |
| Petroselinic acid (0.01M) | 93.7 ± 10.3 |
| EGCG (0.005 μg/ml) | 118.4 ± 3.1 |
| Petroselinic acid (0.01M) + EGCG 0.005 μg/ml | 140.5 ± 16.7 |
| Control | 100.0 ± 3.5 |
| Petroselinic acid (0.01M) | 91.6 ± 5.1 |
| EGCG (0.05 μg/ml) | 111.7 ± 9.9 |
| Petroselinic acid (0.01M) + EGCG 0.05 μg/ml | 131.2 ± 9.2 |
| Control | 100.0 ± 7.7 |
| Petroselinic acid (0.01M) | 102.7 ± 4.5 |
| EGCG (0.5 μg/ml) | 120.2 ± 3.7 |
| Petroselinic acid (0.01M) + EGCG 0.5 μg/ml | 155.9 ± 8.9 |
| Control | 100.0 ± 3.3 |
| Petroselinic acid (0.01M) | 100.9 ± 8.2 |
| Gallic acid (0.001 μg/ml) | 96.6 ± 7.4 |
| Petroselinic acid (0.01M) + Gallic acid 0.001 μg/ml | 129.2 ± 13.9 |
| Genistein (1 μm) | 101.7 ± 2.3 |
| Petroselinic Acid (0.01 μM) | 117.3 ± 4.5 |
| Genistein + Petroselinic acid | 130.2 ± 9.0 |
| 0.1 μM Daidzein | 115.4 ± 5.5 |
| 0.01 μM Petroselinic acid | 104.3 ± 3.0 |
| Daidzein + Petroselinic acid | 130.8 ± 4.4 |

TABLE 3

Synergistic boosting of decorin by petroselinic acid and antioxidants

The production of decorin by fibroblasts was determined in control cells (no treatment) and petroselinic acid and/or antioxidant treated cells. The data is represented as mean +/− standard deviation (n = 3) for decorin levels as a percentage of the control (no antioxidant). A synergistic effect in boosting decorin levels of both antioxidants and petroselinic acid was observed, compared to the control.

5. 80% Fat Examples

Three margarines were produced using exactly the same process conditions.

| A. Formulation | |
| --- | --- |
| Aqueous Phase | |
| Water | 18.48% |
| Potassium Sorbate | 0.15 |
| Citric Acid | 0.07 |
| SMP | 1.0 |
| Fat Phase | |
| Fat Blend | 80.0 |
| Hymono 8903 | 0.3 |

-continued

| A. Formulation | | |
|---|---|---|
| Fat Phase: | Product 1. | 13% InEs, 87% SF (Control) |
| | Product 2. | 13% InEs, 12% Coriander Oil, 75% SF (=according to EP777971) |
| | Product 3. | 13% InEs, 47% Coriander Oil, 40% SF |

InEs = interesterified palmoil 58/palm kernel olein ratio 1:1
Coriander: contained 46 wt % PSA.
SF = sunflower oil B. Process Conditions The process line was configured as:

Premix-Pump-$A_1$-unit-$C_1$-unit-$A_2$-unit

Premix temperature was set at 65° C. and 60-rpm stirrer speed. All units were set to 15 AC, with shaft speeds set to 1000 rpm. Throughput was 50 g/min. using the constant displacement pump. A coarse premix was prepared by slowly adding the prepared aqueous phase to the oil phase in the premix tank. A 2 kg-batch size was employed. The mix was allowed to stir for 15 minutes before pumping was commenced. After pumping was started, the line was allowed to run for 15 minutes before any collection of product.

The following process parameters were noted:

| Product | $A_1$ exit (° C.) | $C_1$ exit (° C.) | $A_2$ exit (° C.) | Line Pressure (bar) |
|---|---|---|---|---|
| 80% Fat Control | 20.1 | 18.4 | 18.4 | 1.5 |
| 80% Fat, 12% Coriander | 20.6 | 18.5 | 18.4 | 1.3 |
| 80% Fat, 47% Coriander | 20.8 | 18.6 | 18.4 | 1.4 |

Five tubs of each product were collected and placed at 5° C. After one day, one tub of each was transferred to each of 5°, 10°, 15° and 20° C. for evaluations after one week.

6. Product Assessment

Product 3 (47% Coriander) was pale yellow in colour, with the others being very white.

All samples spread easily and smoothly, with no water loss evident. No difference in taste was found between samples. Good breakdown in the mouth was evident for all samples.

| Sample | C-Value (g/cm²) | Collar (Scale I to VI) | Conductivity ($\mu$Scm$^{-1}$) |
|---|---|---|---|
| 5° C. Storage | | | |
| 1. 80% Fat Control | 725 | II | <10$^{-5}$ |
| 2. 80% Fat, 12% Coriander | 675 | II | <10$^{-5}$ |
| 3. 80% Fat, 47% Coriander | 750 | II | <10$^{-5}$ |
| 10° Storage | | | |
| 1. 80% Fat Control | 580 | II | <10$^{-5}$ |
| 2. 80% Fat, 12% Coriander | 560 | II | <10$^{-5}$ |
| 3. 80% Fat, 47% Coriander | 590 | II | <10$^{-5}$ |
| Coriander 15° C. Storage | | | |
| 1. 80% Fat Control | 380 | I | <10$^{-5}$ |
| 2. 80% Fat, 12% Coriander | 360 | I | <10$^{-5}$ |
| 3. 80% Fat, 47% Coriander | 410 | I | <10$^{-5}$ |
| 20° C. Storage | | | |
| 1. 80% Fat Control | 360 | I | <10$^{-5}$ |
| 2. 80% Fat, 12% Coriander | 340 | I | <10$^{-5}$ |
| 3. 80% Fat, 47% Coriander | 330 | I | <10$^{-5}$ |

C-value Measurement

C-values are determined using a cone penetrometer (manufactured by SUR) and a 40° cone (weight 80 g). The point of the cone is placed just in contact with the surface of the spread and the cone allowed to drop for 5 seconds. The distance travelled is thus proportional to the hardness of the product.

The C-value can then be calculated from $C = K.F/P^{1.6}$
Where
C=Yiel or C-value in (g/cm²)
F=Total weight of cone and sliding stem (g)
P=Penetration depth (0.1 mm)
K=Fatctor for cone angle (40°=5840)

Conductivity

Conductivity is measured using a cell manufactured by URL Vlaardingen consisting of two parallel plates 1 cm apart, approximately 3×2 cm in size. This is connected to a Philips PW 9526 digital conductivity meter. Conductivity can then be directly read off (in $\mu$Ssm$^{-1}$) after inserting the probe into the spread.

Collar

Collar is measured by inserting a 5 mm diameter steel rod to a depth of 10 mm into the spread. The resulting raising of spread around the rod is graded on a scale of I to VI, with I meaning no raising of product around the rod. VI indicating large amounts of spread raised and cracking of the product around the rod.

7. 40% Fat Examples

Two halvarines were produced, one with coriander oil and a control without.

| a. Formulation | | |
|---|---|---|
| Aqueous Phase | | |
| Water | | 56.48% |
| Potassium Sorbate | | 0.15 |
| Citric Acid | | 0.07 |
| Gelatine (240 bloom) | | 1.5 |
| SMP | | 1.5 |
| Fat Phase | | |
| Fat Blend | | 40.0 |
| Hymono 7804 | | 0.3 |
| Fat Phase: | Product 1. | 13% InEs, 87% SF (Control) |
| | Product 2. | 13% InEs, 42% Coriander Oil, 45% SF | b. Process Conditions

The process line was configured as:

Premix-Pump-A₁-unit-C₁-unit-A₂-unit-C₂-unit

Premix temperature was set at 65° C. and 60-rpm stirrer speed. A-units were set to 10° C., with shaft speeds set to 1000 rpm. C-units were set at 15° C., also with shaft speeds of 1000 rpm. Throughput was 30 g/min. using the constant displacement pump. A coarse premix was prepared by slowly adding the prepared aqueous phase to the oil phase in the premix tank. A 2 kg-batch size was employed. The mix was then allowed to stir for 15 minutes before pumping was commenced. After pumping was started, the line was allowed to run for 15 minutes before any collection of product.

The following process parameters were noted:

| Product | $A_1$ exit (° C.) | $C_1$ exit (° C.) | $A_2$ exit (° C.) | $C_2$ exit (° C.) | Line Pressure (bar) |
|---|---|---|---|---|---|
| 40% Fat Control | 21.1 | 16.5 | 18.3 | 13.8 | 3.5 |
| 40% Fat, 42% Coriander | 22.6 | 17.3 | 18.5 | 13.9 | 3.8 |

Five tubs of each product were collected and placed at 5° C. After one day, one tub of each was transferred to each of 5°, 10°, 15° and 20° C. for evaluations after one week.

C. Product Assessment

The 42% Coriander sample was slightly more yellow in colour than the control, but not as marked a difference as with the margarine.

All samples spread easily and smoothly, with no water loss evident. No difference in taste was found between samples. Good breakdown in the mouth was evident for all samples. Improved hardness was found at 5° C., this is beneficial to make low fat products with reduced levels of hardstock.

| Sample | C-Value (g/cm²) | Collar Scale I to VI | Conductivity (µScm⁻¹) |
|---|---|---|---|
| 5° C. Storage | | | |
| 1. 40% Fat Control | 410 | II | <10⁻⁴ |
| 2. 40% Fat, 42% Coriander (on fat) | 600 | II | <10⁻⁴ |
| 10° Storage | | | |
| 1. 40% Fat Control | 400 | II | <10⁻⁴ |
| 2. 40% Fat, 42% Coriander (on fat) | 410 | II | <10⁻⁴ |
| 15° C. Storage | | | |
| 1. 40% Fat Control | 240 | I | <10⁻⁴ |
| 2. 40% Fat, 42% Coriander (on fat) | 250 | I | <10⁻⁴ |
| 20° C. Storage | | | |
| 1. 40% Fat Control | 230 | I | <10⁻⁴ |
| 2. 40% Fat, 42% Coriander (on fat) | 250 | I | <10⁻⁴ |

8. Ice Cream

The ice creams were made according to the following recipes.

| Recipe: | Wt % |
|---|---|
| Fat blend | 10 |
| Skimmed milkpowder | 10 |
| Icing sugar | 12 |
| Corn syrup solids | 4 |
| Dextrose monohydrate | 2 |
| Dimodan PVP | 0.6 |
| Water | 61.4 |

The fat blend for the reference no1 was 30% POf IV65/20% CN/50% SF and the fatblend according to the invention no 2 was 30% POf IV65/20% CN/50% Coriander.

POf IV 65=palm olein Iodine value: 65

CN=coconut oil

Processing

All ingredients except the water and the fat were mixed. Then the cold water was added to this mixture. This mixture was heated in a water bath to a temperature of 70° C. Then the fully liquid fat blend comprising the palm oleine (PO-f), coconut oil (CN) and sunflower oil (SF) (=reference) or Coriander oil (blend 2) was added to the mixture and was stirred in the ultra-turrax. This emulsion was cooled in a water bath of 20° C. The emulsion was stirred in the ultra-turrax again. The batch ice cream machine was held for 24 hours at −28° C. prior to use. The emulsion was placed in the batch ice cream machine and was stirred for 15 minutes. The resulting ice cream was stored at −18° C. for 3 days and was then evaluated.

Evaluation

The following evaluations were performed:

Processing of the materials

Viscosity measurement of the ice cream emulsion prior to freezing at 20° C. Method: Haake viscometer using Casson regression method.

Overrun directly after freezing. Method: Standardized amount of product is weighed before and after freezing/aeration process to determine amount of air incorporated into the product during freezing/aeration process (overrun measured in % air on total weight)

Hardness of the ice cream after storage for 3 days in the freezer Method: Stevens texture analyzer using 60° cone, Speed 0.5 mm/sec and penetration depth 2 mm. Hardness measured in grams Sensory evaluation (hardness, texture, melt down and flavor release)

Results ice cream preparation

Both ice creams could be processed using standard equipment.

| | 1 | 2 |
|---|---|---|
| Viscosity ice at 20° C. | | |
| Eta (Pas) | 0.008174 | 0.009123 |
| Tau0 (Pa) | 0.111 | 0.05834 |
| Cupweight at 20° C. (g) | 70.1 | 73 |

| | Temp (° C.) | Cupweight (g) | Temp (° C.) | Cupweight (g) |
|---|---|---|---|---|
| 0 min | 6.1 | 94.8 | 6.3 | 92.9 |
| 20 min | −4.5 | 87.4 | −4.5 | 88.4 |

|  |  |  |  |
|---|---|---|---|
| 3 days freezer | −18 | 86.5 | −18 | 86.7 |
| Overrun % |  | 9.6 |  | 7.2 |

Hardness after 3 days in the freezer

|  |  |
|---|---|
| 1 | 2 |
| 76 | 90 |

Sensory Evaluation

The two ice creams were evaluated by the taste panel after 2 weeks storage at −18° C. The results were as follows:
- Hardness: the sample was slightly harder than the reference
- Meltdown was similar
- Texture: Sample was slightly more grainy, and stayed longer firm.

In general the ice cream samples were of good quality. They were firm, had good texture and oral melt.

9. Bakery Application

Experimental

Reference for bakery application is "Biskien Zacht". The following blends were made:

| Blend: | 1 | 2 | 3 | Ref |
|---|---|---|---|---|
| SHs | 30 | 40 | 50 |  |
| POf IV65 | 25 | 20 | 15 |  |
| Coriander oil | 45 | 40 | 35 |  |
| Biskien zacht$^R$ Ref |  |  |  | 100 |
| NMR us |  |  |  |  |
| N10 | 27.8 | 37.2 | 47.5 | 58 |
| N20 | 17.7 | 26.9 | 35.6 | 36 |
| N25 | 8.3 | 17 | 25.5 | 25 |
| N30 | 2.8 | 7.7 | 14.4 | 14 |
| N35 | 0.5 | 1 | 1.4 | 5 |

SHs=shea stearin

The reference and the best match (blend 3) were evaluated in a standard biscuit recipe.

Recipe
1 Biskien zacht$^R$
2 SHs/POfIV65/Coriander oil 50/15/35

|  | (%) |
|---|---|
| Water | 5.12 |
| Fat | 29.0 |
| Sugar | 23.9 |
| Sodiumbicarbonate | 0.34 |
| Lemon peel | 0.68 |
| Flour | 41 |
|  | 100 |

Processing

The dough was prepared in advance and kept in the refrigerator for 1 night according to the following procedure. Sugar and fat were mixed to smooth mass and then sugar, lemon peel and flour were added to this mixture. Finally the water was added.

The biscuits were baked during 18 minutes at 155° C.

Evaluation

Dough could be processed using standard equipment and the product had acceptable sensory properties.

10. Confectionery

Recipe

The following recipe was used for the evaluation of the fat blends in a filling application:

|  |  |
|---|---|
| Fat blend | 35 |
| Cocoa powder | 10 |
| Skimmed milk powder | 7 |
| Sugar | 48 |
| Lecithin | 0.5 |

The blends to be evaluated were:
1. 40/10/50 CCBs/POfIV65/SF (Reference)
2. 40/10/50 CCBs/POfIV65/Coriander oil
3. 40/60 CCBs/Coriander oil CBs is cocoa butter stearine Processing The fillings were prepared using roller refiner and conche. The fillings were cooled to 29° C. before depositing in aluminium cups.

The Fillings Were Evaluated On

Hardness was measured by use of the Stevens Texture Analyser after (STA) 3 days at 20° C., Cone 60°, penetration 2 mm:

|  | Fat type | STA (g) |
|---|---|---|
| 1 | 10/10/50 CCBs/POfIV65/SF (Ref) | 179 |
| 2 | 40/10/50 CCBs/POfIV65/Coriander oil | 288 |
| 3 | 40/60 CCBs/Coriander oil | 344 |

Sensory Properties

Sample 2 looked like the reference and was slightly softer. Sample 1 and 2 were more chewy and more plastic. Sample 3 was harder, less plastic, not chewy and melted quicker and cooler. This sample was less waxy and had slightly more viscosity of melt.

Composition of Fat Blends Used

| Components | SAFA | Unsat. Sym | Unsat. asym |
|---|---|---|---|
| POf | 40 | 60 | 0 |
| CN | 94 | 6 | 0 |
| SF | 13 | 87 | 0 |
| Coriander | 5 | 33 | 60 |
| SHs | 64 | 36 | 0 |
| CCBs | 66 | 34 | 0 |
| Biskien zacht | n.m. | n.m. | 0 |

Ex 8.1=30/20/50 POf/CN/SF
Ex 8.2=30/20/50 POf/CN/Coriander oil
Ex 9.1=Biskien zacht$^R$
Ex 9.2=50/15/35 SHs/POf/Coriander oil
Ex 10.1=40/10/50 CCBs/POf/SF Ex 10.2=40/10/50 CCBs/POf/Coriander oil
Ex 10.3=40/60 CCBs/Coriander oil

|      | SAFA  | Unsat. Sym | Unsat asym |
|------|-------|------------|------------|
| 8.1  | 37.3  | 62.7       | 0          |
| 8.2  | 33.3  | 35.7       | 30         |
| 9.1  | n.m.  | n.m.       | 0          |
| 9.2  | 39.75 | 38.55      | 21         |
| 10.1 | 36.9  | 63.1       | 0          |
| 10.2 | 32.9  | 36.1       | 30         |
| 10.3 | 29.4  | 33.4       | 36         |

What is claimed is:

1. An edible encapsulated composition with anti-inflammatory and/or anti-aging properties comprising a petroselinic acid containing composition and an anti-oxidant wherein the encapsulating material is selected from the group consisting of: polysaccharides, sugars, fats, proteins and amino acids.

2. An edible encapsulated composition with anti-inflammatory and/or anti-aging properties comprising a petroselinic acid containing composition and an anti-oxidant according to claim 1 wherein the encapsulating material is present in an amount of 5–95 wt % on basis of total encapsulated composition.

3. A method of obtaining at least one effect from the group consisting of an anti-inflammatory effect that inhibits the production of metabolites of arachidonic acid and/or reduces the formation of intracellular adhesion molecules and an anti-aging effect on skin conditions which comprises orally administrating to a subject in need of such effect, an edible composition comprising an effective amount of petroselinic acid together with an anti-oxidant.

4. The method of claim 3 wherein the composition is a functional food composition or a food supplement.

5. The method of claim 3 wherein the composition is administered to obtain a desirable effect on skin conditions selected from the group consisting of wrinkling, sagging, photodamaged skin, dry skin, flaky skin and age spots.

6. The method of claim 3 wherein the composition comprises 5–99.9 wt % of fat or fat blend.

7. The method of claim 6 wherein said composition includes a fat selected from the group consisting of: cocoa butter, palm oil or fractions thereof, palm kernel oil or fractions thereof, interesterified mixtures of the above fats, hardened fats or fractions thereof, sunflower oil, high oleic sunflower oil, soybean oil, rape seed oil, cotton seed oil, safflower oil, high oleic safflower oil, maize oil, MCT oils, hardened liquid oils or fractions thereof and mixtures thereof.

8. The method of claim 3 wherein said composition contains 2–80 wt % of petroselinic acid.

9. The method of claim 8 wherein said composition contains 5–40 wt % of petroselinic acid.

10. The method of claim 3 wherein the petroselinic acid is in the form of its free fatty acid, or a mono-, di- or triglyceride with at least one petroselinic acid group, a wax ester of petroselinic acid or a short alkyl ester of petroselinic acid or mixture thereof.

11. The method of claim 3 wherein said anti-oxidant is selected from the group consisting of natural or synthetic tocopherols, natural polyphenols, BHT, BHA, free radical scavengers and enzymes with anti-oxidant properties.

12. The method of claim 11 wherein said anti-oxidant is a tea extract.

13. A composition comprising:

(1) a fat composition comprising asymmetric isomers from cis monounsaturated fatty acid(s), wherein the fat composition comprises 15–75 wt % of asymmetric isomers from petroselinic acid, 25–50 wt % of saturated fatty acids with 12–24 carbon atoms and 0–60 wt % of isomers of other fatty acids with at least 18 carbon atoms; and (2) from 0.01–5 wt % of one or more anti-oxidants selected from the group consisting of: natural or synthetic tocopherols, natural polyphenols, BHT, BHA, free radical scavengers and enzymes with anti-oxidant properties.

14. A composition according to claim 13 wherein the fat composition (1) comprises three components A, B and C, wherein:

A has a content of asymmetric isomers from monounsaturated fatty acids of at least 20 wt %;

B has a solid fat content, measured on an unstabilized fat by NMR, at 20° C. of at least 20, and C has a content of fatty acids with at least 18 C atoms and a cis 9 double bond of at least 40 wt %, while components A, B and c are present in amounts of:

15–90 wt % of A,

10–85 wt % of B, and

0–75 wt % of C.

15. A composition according to claim 14 wherein the fat composition (1) contains an additional component D in an amount of 5–60 wt %, which component D is an interesterified mixture of fats A and B in a weight ration of 95:5–5:95.

16. A composition according to claim 13 wherein the fat composition has a solid fat content unstabilized at 5° C. of 25–85 and at 35° C. of less than 10.

17. A composition according to claim 14 wherein A is selected from the group consisting of coriander oil, parsley oil or fungal oils.

18. A composition according to claim 14 wherein A is a fat obtained after performing an enrichment in cis 6 isomers of fatty acids of monounsaturated fatty acids by performing an enzymic conversion on a fat containing at least 5 wt % of cis 6 isomers of fatty acids of monounsaturated fatty acids and containing also cis 9 double bonds using an enzyme specific for cis 9 double bonds and removal of the products enriched in cis 9 double bonds.

19. A composition according to claim 13 wherein the fat composition (1) has a trans content of 10–70 wt %.

20. A composition according to claim 14 wherein fat B is selected from the group consisting of: palm oil stearin, palm oil mid; cocoa bufter, cottonseed stearin, fully or partially hardened vegetable oils.

21. A composition according to claim 14 wherein fat C is selected from the group consisting of sunflower oil, high oleic sunflower oil, olive oil, bean oil, safflower coil, rape seed oil, palm oil olein, olein fractions of vegetable oils, high oleic vegetable oils, corn oil or cottonseed oil.

22. A food product having added thereto a composition according to claim 13.

* * * * *